United States Patent [19]

Shen et al.

[11] Patent Number: 5,399,683
[45] Date of Patent: Mar. 21, 1995

[54] MIRROR AMIDE CORD FACTORS AND MIRROR THIOESTER CORD FACTORS FOR DIAGNOSIS OF TUBERCULOSIS

[75] Inventors: Yaping Shen, Vancouver; Hassan Salari, Ladner, both of Canada

[73] Assignee: Inflazyme Pharmaceuticals, Inc., Vancouver, Canada

[21] Appl. No.: 63,542

[22] Filed: May 19, 1993

[30] Foreign Application Priority Data

Mar. 26, 1993 [CA] Canada .................... 2092731

[51] Int. Cl.$^6$ .................... C07H 3/04; G01N 33/545
[52] U.S. Cl. .................... 536/123.13; 435/7.94; 536/124
[58] Field of Search .................... 536/123.13, 124

[56] References Cited

U.S. PATENT DOCUMENTS

| | | |
|---|---|---|
| 2,332,521 | 10/1943 | Maswool . |
| 3,135,662 | 6/1964 | Pope et al. . |
| 3,452,135 | 6/1969 | Medveczky .................... 424/9 |
| 3,493,652 | 2/1970 | Hartman .................... 424/94 |
| 3,522,347 | 7/1970 | Ablondi et al. .................... 424/92 |
| 3,678,149 | 7/1972 | Prigal .................... 424/8 |
| 3,752,886 | 8/1973 | Munder et al. .................... 424/199 |
| 3,767,790 | 10/1973 | Guttag . |
| 3,787,571 | 1/1974 | Higuchi . |
| 3,814,097 | 6/1974 | Ganderton et al. . |
| 3,837,340 | 9/1974 | Counter .................... 424/89 |
| 3,859,435 | 1/1975 | Bruzzese et al. . |
| 3,937,815 | 2/1976 | Bruzzese et al. .................... 435/228 |
| 3,962,414 | 6/1976 | Michaels . |
| 4,004,979 | 1/1977 | Avrameas et al. .................... 436/823 |

(List continued on next page.)

FOREIGN PATENT DOCUMENTS 1572368 6/1977 United Kingdom .

OTHER PUBLICATIONS

Rosenberg et al., "Effect of topical applications of heavy suspensions of killed *Malassezia ovalis* on rabbit skin", Mycopathologia 72, 147–154 (1980).

De Briel, et al., "High-performance liquid chromatography of corynomycolic acid as a tool in identification of *Corynebacterium* species and related organisms", Journal of Clinical Microbiology, Jun. 1992, pp. 1407–1417.

De Briel, et al., "Contribution of High-performance liquid chromatography to the identification of some *Corynebacterium* species by comparison of their corynomycolic acid patterns", Res. Microbiol., 1992, 143, 191–198.

Liav et al., "Synthesis of 6,6'-di-O-mycoloyl- and corynomycoloyl-(α-D-galactopyranosyl α-D-galac- (List continued on next page.)

*Primary Examiner*—Mary E. Ceperley
*Attorney, Agent, or Firm*—Nixon & Vanderhye

[57] ABSTRACT

A "mirror" amide cord factor or "mirror" thioester cord factor having the following generic formula:

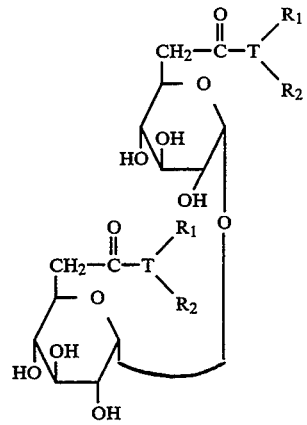

is alkyl having 8 to 90 carbons or alkoxy having 8 to 90 carbons, and $R_2$ is hydrogen, alkyl having 8 to 90 carbons or alkoxy having 8 to 90 carbons; and when T is sulphur, $R_1$ is alkyl having 8 to 90 carbons or alkoxy having 8 to 90 carbons and $R_2$ is absent.

5 Claims, No Drawings

U.S. PATENT DOCUMENTS

| | | | |
|---|---|---|---|
| 4,022,878 | 5/1977 | Gross | 436/815 |
| 4,057,685 | 11/1977 | McIntire | 530/363 |
| 4,122,158 | 10/1978 | Schmitt | 514/157 |
| 4,164,560 | 8/1979 | Folkman et al. | 435/182 |
| 4,166,800 | 9/1979 | Fong . | |
| 4,243,663 | 1/1981 | Azuma et al. | 514/53 |
| 4,307,229 | 12/1981 | Liav et al. | 514/924 |
| 4,340,586 | 7/1982 | Bekierkunst et al. | 424/92 |
| 4,340,588 | 7/1982 | Woodard | 424/92 |
| 4,454,119 | 6/1984 | Fukushi | 514/53 |
| 4,484,923 | 11/1984 | Amkraut et al. . | |
| 4,612,304 | 9/1986 | Fukushi | 514/53 |

OTHER PUBLICATIONS topyranoside) via triflates", Chemistry and Physics of Lipids, 51 (1989) 9–13.

Thuioshi Ioneda, "Separation of homologues of methyl ester and 3-O-acetyl methyl ester derivatives of the corynomycolic acid fraction from *Corynebacterium pseudotuberculosis*", Journal of Chromatography, 481 (1989) 411–415.

Utaka, et al., "Asymmetric Reduction of 3-Oxo-octadecanoic Acid with Fermenting Baker's Yeast. An Easy Synthesis of Optically Pure (+)-(2R,3-R)-Corynomycolic Acid", J. Chem. Soc., Chem. Commun., 1987, 1368–1369.

Gobbert, et al., "Microbial Transesterification of Sugar-Corynomycolates", JAOCS, vol. 65, No. 9 (Sep. 1988), 1519–1525.

Laszlo, et al., "Evaluation of synthetic pseudo cord-factor-like glycolipids for the serodiagnosis of tuberculosis", Res. Microbiol. 1992, 143, 217–223.

Cruaud, et al., "Human IgG Antibodies Immunoreacting with Specific Sulfolipids from *Mycobacterium tuberculosis*", Zbl. Bakt. 271, 481–485 (1989).

McNeil, et al., "Evidence for the Nature of the Link between the Arabinogalactan and Peptidoglycan of Mycobacterial Cell Walls", Jour. Biol. Chem., 1990, vol., 265, 18200–18206.

Daffe, et al., "Predominant Structural Features of the Cell Wall Arabinogalactan of *Mycobacterium tuberculosis* as Revealed through Characterization of Oligoglycosly Alditol Fagments by Gas Chromatography/Mass Spectrometry and by H and C NMR Analyses", Jour. Biol. Chem., 1989, 6734–6743.

Baer and Breton, "Synthesis of alkyl [(alkyl 6-deoxy-α-D-gluco-deptopyranosyl-uronate) 6-deoxy-α-D-gluco-deptopyranosid]uronates, a novel type of mirror pseudo cord factor", Carbohydrate Research, 209 (1990) 181–189.

Baer, et al., "Synthesis of a trehalose homolog, 6-deoxy-α-D-gluco-deptopyranosyl 6-deoxy-α-D-gluco-deptopyranoside, and the corresponding bis(heptosiduronic acid)", Carbohydrate Research, 200 (1990) 377–389.

Reggiardo and Middlebrook, "Serologically active glycolipid families from *Mycobacterium bovis* BCG", Amer. Jour. of Epidemiology, vol. 100, No. 6, 1975, 469–486.

Daffe, et al., "Glycolipids of Recent Clinical Isolates of *Mycobacterium tuberculosis*: Chemical Characterization and Immunoreactivity", Jour. of Gen. Microbiology (1989), 135, 2759–2766.

Cruaud, et al., "Evaluation of a novel 2,3-diacyl-trehalose-2'-sulphate (SL-IV) antigen for case finding and diagnosis of leprosy and tuberculosis", Res. Microbiol., 1990, 141, 679–694.

Hack's Chemical Dictionary, McGraw-Hill, Inc., New York, Fourth Edition, edited by Julius Grant (1969), p. 27.

R. Morrison et al., Organic Chemistry, second edition (1967), pp. 591 and 1113.

MIRROR AMIDE CORD FACTORS AND MIRROR THIOESTER CORD FACTORS FOR DIAGNOSIS OF TUBERCULOSIS

FIELD OF THE INVENTION

This invention relates to the use of novel mirror amide cord factors and mirror thioester cord factors for the diagnosis of tuberculosis.

BACKGROUND OF THE INVENTION

At one time, it was thought that the debilitating, and often deadly, disease known generically as tuberculosis had been conquered as an anathema to mankind. Unfortunately, recent data indicates that the incidence of tuberculosis in humans has not been eradicated but is becoming more prevalent.

In treating humans afflicted with tuberculosis, the length of treatment and minimization of damage to the lungs is directly dependent upon early diagnosis of the condition. The earlier the diagnosis, the shorter the treatment term and the less the damage. Traditionally, it has been common medical practice to clinically diagnose tuberculosis in the lungs of a human being by a number of techniques including chest X-rays and cultures grown from sputum of the patient. Tuberculosis is a condition caused in the lungs by *Mycobacterium tuberculosis*. Regrettably, the tuberculosis condition in the lungs must be relatively well advanced before symptoms show up in the patient. Typical symptoms are coughing sputum and pains in the chest area. When the symptoms appear, diagnosis procedures are conducted clinically. Spots on the lung noted by chest X-rays, and clinical cultures developed in the laboratory, microscopic analysis of sputum of afflicted patients, are not reliable until the tuberculosis condition is relatively well advanced.

There is a strong need for a reliable procedure for early diagnosis of tuberculosis. Hopes of developing useful serodiagnostic tests for tuberculosis were heightened recently by the discovery of a *Mycobacterium tuberculosis* species-specific trehalose-containing glycolipid provisionally designated as SL-IV (Papa et al., 1989; Cruaud et al., 1990). This compound was originally thought to bear a sulphate ester group in position 2' (Daffe et al., 1990); however, a recently completed reinvestigation of the structure failed to confirm the presence of sulphate (Baer, personal communication). An ELISA serological procedure using this 2,3-O-diacyltrehalose has been shown to have good potential in the diagnosis of tuberculosis and leprosy (Cruaud et al., 1990).

Trehalose-based glycolipids are found in a variety of structural forms in the lipids of mycobacteria and related bacteria. Serologically active glycolipids extracted from *M. bovis* BCG have been described (Reggiardo and Middlebrook, 1975a,b). Three families of glycolipids called A, B and C reacted with sera from patients with tuberculosis and leprosy. Among the antigens studied, one designated A1 gave the lowest incidence of false-negative serologic reactions and was proved to be 6-o-mycoloyltrehalose or TMM (Reggiardo et al., reported in Goren, 1990). Cord factor (6,6'-di-o-mycoloyltrehalose (TDM)), on the other hand, does not seem to be useful as a coating antigen (Goren, 1990). Pseudo cord factors in which the carbon atoms C-6 and C-6' of the trehalose have been transformed either to carboxylic esters or to carboxamide functions, have been synthesized. Some of them, notably acylated dideoxydiamino derivatives, exhibit greater toxicity in mice than the simple cord factor analogue 6,6'-di-o-palmitoyltrehalose or the cord factor itself (Goren, 1990). A recent report shows that a neoglycoconjugate of bovine serum albumin (BSA) containing similar pseudo antigens was useful in the serodiagnosis of coccidioidomycosis (Goren et al., 1990). Among other biological characteristics, cord factors and their synthetic, albeit simpler analogues, induce granuloma formation in mice and have anti-tumour activity (Bekierkunst, 1984).

An article entitled "Evaluation of synthetic pseudo cord-factor-like glycolipids for the serodiagnosis of tuberculosis", Res. Microbiol. 1992, 143, 217–223, A. Laszlo et al., discloses five glycolipids which were evaluated in an ELISA test for their serodiagnostic usefulness in tuberculosis. One hundred and twelve (112) sera belonging to bacteriologically confirmed TB patients, patients with pathologies other than tuberculosis and healthy individuals were examined against several synthetic "mirror" pseudo cord factors (analogues of trehalose-6,6'-dimycolate or TDM) using natural cord factor and another recently described natural glycolipid (SL-IV) of *Mycobacterium tuberculosis* as control antigens. Analysis of the results showed that all synthetic "mirror" pseudo cord factors, except one with a short-8-carbon chain, were better recognized by the sera of tuberculosis patients than natural cord factor, with sensitivity and specificity values in the ELISA test similar to those reported for *M. tuberculosis* species-specific SL-IV.

Of all antigens tested in that study, BDA.TDA, a bis(N,N-dioctadecylamide) of "trehalose dicarboxylic acid", [($\alpha$-D-glucopyranosyluronic acid) ($\alpha$-D-glucopyranosiduranic acid)], showed the highest serodiagnostic discriminating power (93% sensitivity and specificity). It was postulated that either these artificial molecules are cross-reactants of similarly structured native glycolipids of *M. tuberculosis* or that they bear closer resemblance to actual phagosome-lysosome-modified antigens than to native mycobacterial ones.

Seven antigens were tested, namely, five bisalkyl esters (I) of "homotrehalosuronic acid" (6-deoxy-$\alpha$-D-gluco-heptopyranosyluronic acid, 6-deoxy-$\alpha$-D-glucoheptopyranosiduronic acid) were synthesized as described (Baer and Breton, 1991; Baer et al., 1990). Differing in the length of their lipid chains R, they represent a novel type of "mirror" pseudo cord factor structure. The "mirror amide" pseudo cord factor (II) was synthesized. It is trehalose dicarboxylic acid bis (N,N-dioctadecylamide) (BDA.TDA). Cord factor (III, TDM) "Peurois" was originally obtained from the late Dr. E. Lederer. The SL-IV (Daffé et al., 1989; Cruaud et al., 1989) obtained from the Pasteur Institute, were used as natural *M. tuberculosis* antigens for reference.

Test data for the seven different antigens varied considerably. The sensitivity and specificity of the antigen showing the highest serodiagnostic discriminating power (93 percent), namely, BDA.TDA, a bis (N,N-dioctadecylamide) of trehalose dicarboxylic acid [($\alpha$-D-glucopyranosiduronic) ($\alpha$-D-glucopyranosiduranic acid)] was more than double the bis-alkyl ester having the substituent n-$C_{15}H_{31}$, pentadecyl, and almost three times the data for TDM, which incorporated the substituent mycoloyl. These data demonstrate that it is not possible to predict with any reliability the sensitivity and specificity of such antigens without conducting specific tests. The predictability factor in endeavouring to extrapolate the effectiveness of one antigen, based on homologues or similar organic structures, is minimal.

SUMMARY OF THE INVENTION

We have synthesized a series of novel bis-alkyl ester structures incorporating nitrogen and sulphur substituents of "homotrehalosuronic acid" (6-deoxy-α-D-gluco-heptopyranosuronic acid (6-deoxy-α-D-gluco-heptopyranosiduronic acid) which demonstrate strong sensitivity and specificity in the serodiagnosis of tuberculosis.

Our invention includes a process of preparing a compound of the following formula:

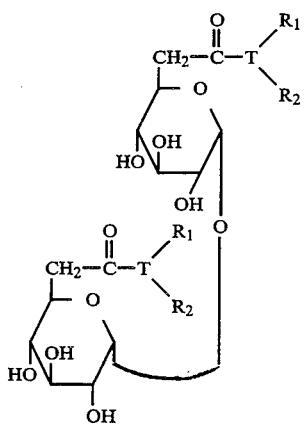

wherein T is nitrogen or sulphur, $R_1$ is an alkyl group having 8 to 90 carbons or an alkoxy group having 8 to 90 carbons, and $R_2$ is hydrogen or the same as $R_1$, which comprises reacting a 2,3,4-tri-O-benzyl-6-deoxy-α-D-gluco-heptoapyranosyluronic acid (2,3,4-tri-O-benzyl-6-deoxy-α-D-gluco-heptopyranosiduronic acid of the formula

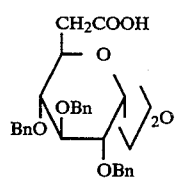

wherein Bn represents benzyl. Treatment of the diacid with thionyl chloride or oxalyl chloride to yields an acid chloride of the formula

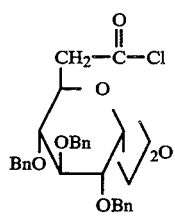

(b) treatment of the acid chloride with

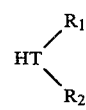

to yield a diamide or dithioester of the formula

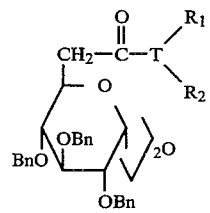

(c) debenzylation of the diamide or dithioester in the presence of hydrogen/Pd-C to yield the desired compound.

Our invention also includes a "mirror" amide cord factor or "mirror" thioester cord factor having the following generic formula:

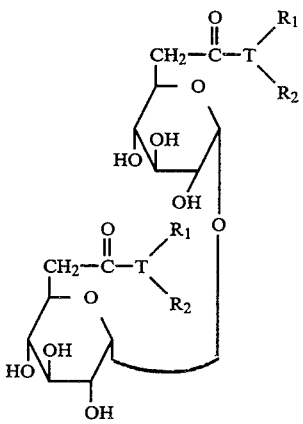

wherein T is nitrogen or sulphur and when T is nitrogen, $R_1$ is an alkyl having 8 to 90 carbon atoms or an alkoxy having 8 to 90 carbon atoms, and $R_2$ is hydrogen or the same as $R_1$; and when T is sulphur, $R_1$ is an alkyl or alkoxy group having 8 to 90 carbons, and $R_2$ is absent.

Our invention also includes a method of diagnosing tuberculosis in a human being by Elisa detection utilizing a mirror amide cord factor or mirror thioester cord factor compound selected from the group of compounds respresented by the following formula:

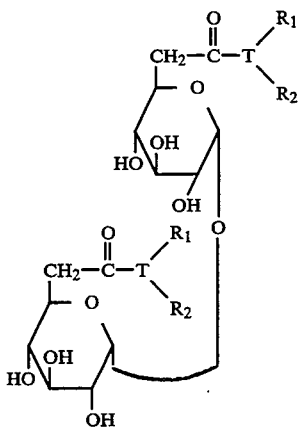

wherein T is nitrogen or sulphur and when T is nitrogen, $R_1$ is an alkyl or alkoxy having 8 to 90 carbons, and $R_2$ is hydrogen or the same as $R_1$; and when T is sulphur, $R_1$ is an alkyl or alkoxy group having 8 to 90 carbons, and $R_2$ is absent.

A method wherein one of the species of the group of compounds is used in the Elisa diagnosis of tuberculosis. Specifically, the method can include a compound of the foregoing generic formula wherein T is nitrogen and $R_1$ and $R_2$ are each $C_{15}H_{31}$.

In the method, two or more of the species of the compounds of the generic formula can be used in the Elisa detection of traces of tuberculosis antibodies in the human being. One or more of the compounds of the general formula can be used in combination with another molecule for the purpose of detection of traces of antibodies against tuberculosis.

In the method: (a) antigen is solubilized in hexane or chloroform and 25 µl volumes of solution containing either 250 or 100 ng of antigen are coated onto polystyrene microtitre plate wells; (b) the plates are dried overnight at room temperature; (c) the wells are treated with hexane alone to check for non-specific adsorption; (d) after saturation overnight at 4° C. with phosphate-buffered saline (PBS), the wells are washed three times with PBS without BSA; (e) sera is diluted 1:100 in containing 0.5% BSA and tested in triplicate; (f) diluted sera (100 µl) is added to the appropriate well and incubated for 90 min. at room temperature; (g) after washings, goat anti-human IgG/peroxidase conjugate (100 µl of 1:100000 dilution) is added and incubated for 2 hours; (h) after further washings, o-Phenyl-enediamine (OPD) dihydrochloride substrate (100 µl of 0.4 mg/ml) is added; (i) the plates are incubated at 37° C. for 60 min.; and (j) the plates are read at 405 nm using an Elisa reader.

The invention is also directed to a "mirror" amide cord factor compound useful for diagnosing tuberculosis in a human being by Elisa detection comprising:

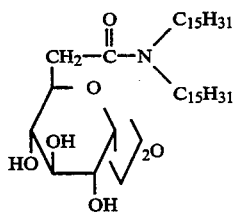

DETAILED DESCRIPTION OF SPECIFIC EMBODIMENTS OF THE INVENTION

Synthesis of the Sugar "Trehalose" Substituent of Novel Synthetic Cord Factor Analogs The novel compounds of the invention are prepared according to the following reactions from (2,3,4-tri-O-benzyl-6-deoxy-α-D-gluco-heptopyranosyluronic acid) 2,3,4-tri-O-benzyl-6-deoxy-α-D-gluco-heptopyranosiduronic acid (compound 1) by reaction with thionylchloride or oxalyl chloride to give its acid chloride (compound 2), followed by nucleophilic attack of the

to yield the diamide or dithioester (compound 3) and followed by debenzylation of the diamide or dithioester in the presence of hydrogen/Pd-C to yield the compounds of the invention (compound 4).

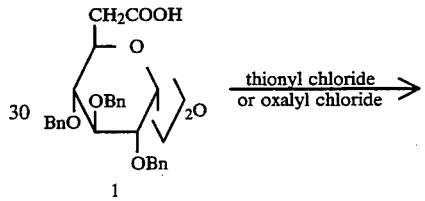

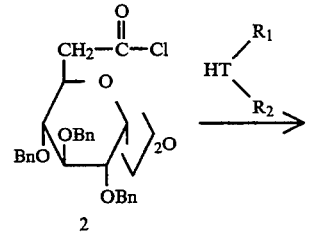

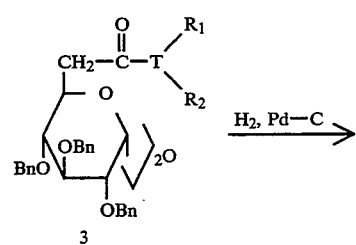

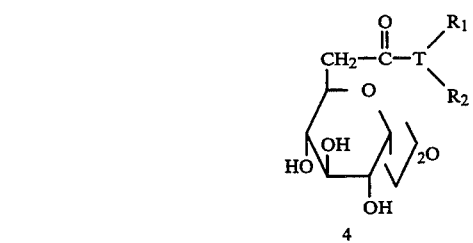

wherein Bn is benzyl, and
wherein T is N (nitrogen), $R_1$ is $C_{8-90}$-alkyl or alkoxy, $R_2$ is $R_1$ or
wherein T is N (nitrogen), $R_1$ is $C_{8-90}$-alkyl or alkoxy, $R_2$ is H, or wherein T is S (sulphur), $R_1$ is $C_{8-90}$-alkyl or alkoxy, $R_2$ is zero.

In specific terms, the synthesis of bis-heptosiduronic acid (2,3,4-tri-O-benzyl-6-deoxy-α-D-glucoheptopyranosyluronic acid); 2,3,4-tri-O-benzyl-6-deoxy-α-D-gluco-heptopyranosiduronic acid (compound 1) was prepared, starting from 2,3,4,2', 3', 4'-hexa-O-benzyl-6,6'-di-O-tosyl-α,α-trehalose.

TB Detection Kit—ELISA

Antigen was solubilized in hexane and 25 μl volumes of solution containing either 250 or 500 ng of antigen were coated onto "Dynatech Immulon 4" polystyrene microtitre plate wells. Plates were dried overnight at room temperature. Wells were treated with hexane alone to check for non-specific adsorption. After saturation overnight at 4° C. with phosphate-buffered saline (PBS), wells were washed three times with PBS without BSA. All sera were diluted 1:100 in containing 0.5% BSA and tested in triplicate. Diluted sera (100 μl) were added to the appropriate well and incubated for 90 min. at room temperature. After washings, goat anti-human IgG/peroxidase conjugate (100 μl of 1:100000 dilution) was added and incubated for 2 hours. After further washings, o-Phenylenediamine (OPD) dihydrochloride substrate (100 μl of 0.4 mg/ml) was added and the plates incubated at 37° C. for 60 min. The plates were read at 405 nm using an ELISA reader.

Absorbance values at 405 nm were determined by subtracting the absorbance of the blank.

ELISA Assay Preparation of Antigen Solution Used to Coat Plates 5 mg of antigen were mixed in 1 ml of chlorform (5 mg/ml stock solution). A 10 ml aliquot of the stock solution was mixed with 990 ml of hexane to give a 50 μg/ml working solution.

To coat the plates plating solutions of 10 and 20 μg/ml.

Assay Protocol

Elisa plate strips (for 8×12 well "Immulon 4" plates) were coated with 25 μl of the 10 and 20 μg/ml plating solutions to coat the wells with 250 and 500 ng antigen respectively.

Plates were dried for approximately 30 min. in a fumehood and then overnight at room temperature.

One strip was coated with hexane alone to check for non-specific adsorption. No non-specific adsorption of the antibody was detected.

PBS containing 5% BSA was added to each well (100 μL). Plates were incubated at 4° C. overnight.

PBS-BSA was removed under vacuum and waste was collected in a vacuum trap. Plates were washed three times with 200 μL PBS containing no added BSA.

Human serum (control and test samples) were diluted 1:100 in PBS containing 0.5% BSA. Aliquots (100 μL) were added to the appropriate wells (measurements in triplicate) and allowed to incubate for 90 min. at room temperature. Three wells were treated with PBS plus 0.5% BSA alone to serve as a no serum blank.

Serum samples in each well were aspirated. Plates were washed with PBS (no added BSA) four times.

Anti-human IgG peroxidase conjugate (Sigma A-0170) was diluted 1:10,000 using PBS.

To each well, 100 μL of the diluted anti-IgG with peroxidase label was added. Samples were incubated for 2 hours.

Substrate solution was prepared as follows. One phosphate-citrate buffer capsule (Sigma P4922) containing 0.03% sodium perborate (substitute for $H_2O_2$) was dissolved in 100 ml water. One 10 mg tablet of o-phenylenediamine (OPD) dihydrochloride (Sigma P-8287) was dissolved in 25 ml of buffer to give a 0.4 mg/ml solution of OPD.

100 μL of substrate solution was added to each well and incubated at 37° C. for 1 hour. O.D. was measured at 405 nm using an Elisa reader.

To demonstrate the effectiveness as diagnostic aids of this novel group of compounds, the inventors have conducted Elisa detection tests on nine patients and six normals utilizing the compounds of the invention. For comparison purposes, and to verify the reliability of the Elisa detection test, accompanying clinical diagnosis tests were conducted on the same patients. The results of these tests are demonstrated in Table I below.

TABLE I

| Patient | ELISA Detection | Clinician Diagnosed |
|---|---|---|
| #1 | ++++ | +++ |
| #2 | ++++ | ++++ |
| #3 | + | + |
| #4 | +++ | + |
| #5 | − | − |
| #6 | + | − |
| #7 | − | − |
| #8 | +++ | +++ |
| #9 | − | − |
| #10 | − | − |
| #11 | − | − |
| #12 | − | − |
| #13 | − | − |
| #14 | − | − |
| #15 | − | − |

+ denotes positive diagnosis. Number of + denotes strength of detection.

The data tabulated in Table I indicates that the Elisa detection for the compounds of the invention were reliable and more sensitive than the clinically conducted diagnosis. For example, patient #6 exhibited a positive Elisa detection result, whereas no detection was discernible conducting the conventional clinical diagnosis procedures. Patient #4 demonstrated a degree of Elisa detection that was basically three times as sensitive as the clinical diagnosis. The Elisa detection for patient #1 displayed four points compared to three points for the clinical procedure. None of the normals had a positive reading. This data tends to demonstrate that the compounds of the invention are useful in detecting the presence of tuberculosis in a patient at an earlier stage than is possible using conventional clinical tuberculosis diagnosis procedures. This is advantageous because early detection of tuberculosis and early treatment enable the tuberculosis condition to be treated more promptly, and for a shorter period of time, thereby resulting in less damage to the lungs.

The tests were done using mirror amide cord factor, where T is nitrogen, and $R_1$ and $R_2$ are $C_{15}H_{31}$ of the formula:

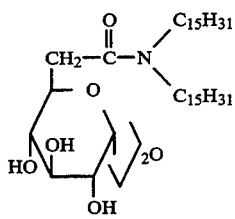

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

APPENDIX A

1. Japanese Patent No. 2,004,798 discloses a group of cord factor analogs as immunoenhancers.
2. U.S. Pat. No. 4,612,304 protects a group of cord factors and trehalose dialkanoate esters as anti-tumor agents.
3. Japanese Patent No. 60,221,097 protects the use of Corynebacterium as a tool for the production of L-lysine. L-lysine is used in the production of pharmaceuticals, food and foodstuffs.
4. U.S. Pat. No. 4,484,923 protects the use of cord factors as immunopotentiators.
5. Japanese Patent Nos. 87,000,131 and 59,089,632 disclose the use of cord factors as adjuvants in the treatment of cancer using immunotherapy.
6. U.S. Pat. No. 4,454,119 protects the use of cord factors as anti-tumor agents when used alone or as an oil-in-water suspension.
7. Canadian Patent No. 1,171,786 protects the use of cord factors in the treatment of cancer.
8. U.S. Pat. No. 4,340,586 protects the use of cord factors in the treatment of skin disorders such as mycosis.
9. U.S. Pat. No. 4,243,663, British Patent No. 1,596,516, French Patent No. 2,399,845 and Japanese Patent No. 54,028,830 disclose a group of glycolipids having the D-fructose sucrose of D-glucose sugar moiety, which are claimed to be useful as immunotherapeutic agents and useful in treating ulcers.
10. Japanese Patent No. 53,003,514, French Patent No. 2,355,506, British Patent No. 15,722,368 and Japanese Patent No. 59,089,632 protect a group of glycolipid adjuvants as vaccine against tumour cells.
11. Several U.S. Pat. Nos. have been granted for the use of cord factor for potentiation of immune response. These include the following: 2,332,521; 3,075,883; 3,135,662; 3,452,135; 3,493,652; 3,522,347; 3,678,149; 3,752,886, 3,767,790; 3,787,571; 3,814,097; 3,837,340, 3,859,435, 3,937,815, 3,962,414; 3,964,482; 3,995,631; 4,004,979; 4,022,878; 4,057,685; 4,122,158; 4,164,560 and 4,166,800.
12. U.S. Pat. No. 4,307,229 claims a novel route for the synthesis of trehalose derivatives without any specific claims for their use.
13. Several research papers discuss the analysis and synthesis of trehalose of the corynomycolic. These include: J. Clin. microbiol. 30(6) 1407-17; Res. Microbiol. 143 (2) 191-8; Chem. Phys. Lipids, 51 (1) 9-13; YUKAGAKU 38 (12) 1001-6; J. Chromatogr. 481, 411-15; J. Chem. Soc., Chem. Commun. (18), 1368-9; and J. Am. Oil Chem. Soc. 65 (9) 1519-25.

What is claimed is:

1. A "mirror" amide cord factor or "mirror" thioester cord factor of the formula:

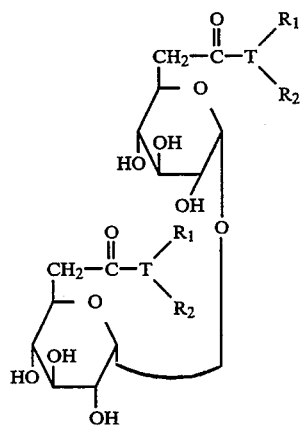

wherein T is nitrogen or sulphur and when T is nitrogen, $R_1$ is alkyl having 8 to 90 carbons or alkoxy having 8 to 90 carbons, and $R_2$ is hydrogen, alkyl having 8 to 90 carbons or alkoxy having 8 to 90 carbons; and when T is sulphur, $R_1$ is alkyl having 8 to 90 carbons or alkoxy having 8 to 90 carbons and $R_2$ is absent.

2. A compound as claimed in claim 1, wherein T is nitrogen, $R_1$ is alkyl having 8 to 90 carbons or alkoxy having 8 to 90 carbons, and $R_2$ is alkyl having 8 to 90 carbons or alkoxy having 8 to 90 carbons.

3. A compound as claimed in claim 1, wherein T is nitrogen, $R_2$ is hydrogen and $R_1$ is alkyl having 8 to 90 carbons or alkoxy having 8 to 90 carbons.

4. A compound as claimed in claim 1, wherein T is sulphur, $R_2$ is absent, and $R_1$ is alkyl having 8 to 90 carbons or alkoxy having 8 to 90 carbons.

5. A "mirror" amide cord factor compound useful for diagnosing tuberculosis in a human being by ELISA detection of the formula:

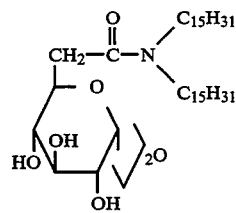

* * * * *